United States Patent [19]

Rasor et al.

[11] 4,442,843
[45] Apr. 17, 1984

[54] MICROBUBBLE PRECURSORS AND METHODS FOR THEIR PRODUCTION AND USE

[75] Inventors: Julia S. Rasor, Cupertino; Ernest G. Tickner, Gilroy, both of Calif.

[73] Assignee: Schering, AG, Berlin, Fed. Rep. of Germany

[21] Appl. No.: 322,138

[22] Filed: Nov. 17, 1981

Related U.S. Application Data

[63] Continuation-in-part of Ser. No. 207,741, Nov. 17, 1980, abandoned.

[51] Int. Cl.$^3$ .............................................. A61G 10/00
[52] U.S. Cl. ........................................ 128/660; 128/661; 128/663; 128/653
[58] Field of Search ................... 73/600, 703; 128/660, 128/662, 663

[56] References Cited

U.S. PATENT DOCUMENTS 4,265,251  5/1981  Tickner ................................ 128/660
4,276,885  7/1981  Tickner et al. ..................... 128/660

FOREIGN PATENT DOCUMENTS 52575  5/1982  Int'l Pat. Institute ............. 128/660

OTHER PUBLICATIONS

Meltzer et al., "The Source of Ultrasound Contrast Effect", Journal of Clinical Ultrasound, pp. 121-127, Apr. 1980.

Primary Examiner—Kyle L. Howell
Assistant Examiner—George Yanulis
Attorney, Agent, or Firm—Millen & White

[57] ABSTRACT

Microbubbles are formed in a liquid, e.g., blood in order to alter the transmission characteristics thereof to electromagnetic and sonic waves transmitted therethrough, by dissolving therein a solid particulate material, preferably as a suspension in a carrier liquid in which the particulate material is at least temporarily stable, the particles of which are substantially free of microbubbles and have a plurality of gas-filled voids communicating with the surface of the particles and providing nuclei for microbubble formation and the ratio of the mass of the particles to the volume of gas in the voids is sufficient to render the liquid in which the particulate material is dissolved supersaturated with respect to the gas in the voids in the area of the liquid surrounding the microbubbles when they are formed.

17 Claims, 1 Drawing Figure

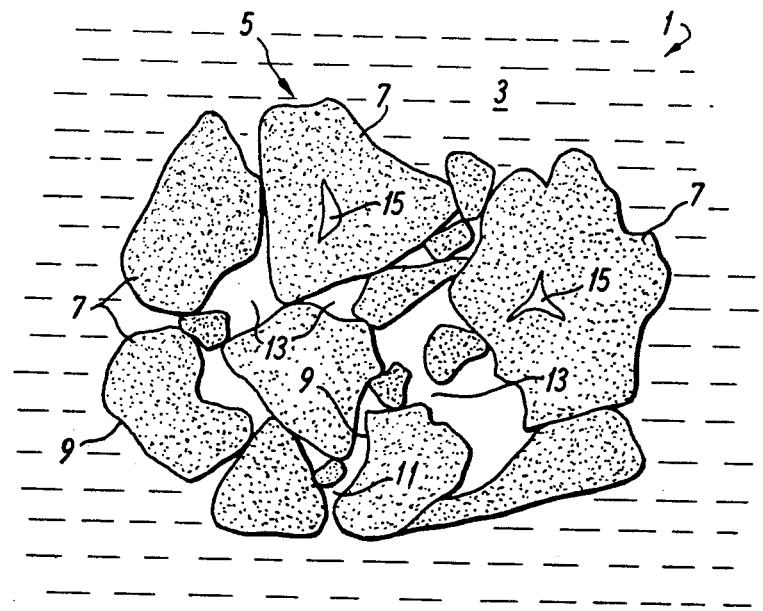

MICROBUBBLE PRECURSORS AND METHODS FOR THEIR PRODUCTION AND USE

This is a continuation-in-part of application Ser. No. 207,741, filed Nov. 17, 1980, now abandoned.

BACKGROUND OF THE INVENTION

This invention relates to novel compositions of matter and articles of manufacture which are useful for generating microbubbles in a liquid, for example, in a liquid filling a vessel or chamber of the human body or a vessel or chamber of an industrial process, to methods of producing such microbubbles and to methods of using the microbubbles thus generated, including the enhancement of ultrasonic images of such liquid filled vessels or chambers containing the microbubbles.

It is known that contrast in ultrasonic images is enhanced by the presence of microbubbles in a liquid, e.g., the blood stream of a test subject. The prior art describes forming such microbubbles both externally of the test subject and then injecting the preformed microbubbles into the subject's blood stream and internally within the blood stream.

For example, microbubbles have been formed by simply vigorously agitating a liquid solution, such as normal saline solution, a dye solution, or a temporarily withdrawn aliquot of blood, prior to its injection into the blood stream. This can lead to significant ultrasonic image contrast enhancement, but these bubbles are generally of non-uniform size, often as large as 2000 microns in diameter which are potentially hazardous as gas emboli. Also, neither the size nor the concentration of the microbubbles can be quantitatively controlled for optimum contrast, thus limiting their usefulness. A method of obtaining microbubbles of a defined size by filtering bubbles produced by applying direct current potential across a silver plate is described in U.S. Pat. No. 3,640,271.

In the method of U.S. Pat. No. 4,276,885, very precise size microbubbles are formed with a coalescence resistant membrane, particularly gelatin, and then the precision microbubbles are injected into the blood stream. This procedure leads to significant image enhancement compared to an aerated saline solution. However, storage of the thus-produced microbubbles requires refrgeration or other techniques which will preserve the microbubbles.

In the procedure of U.S. Pat. No. 4,265,251, a solid microbubble precursor, particularly a saccharide composition having microbubbles of a gas, generally a pressurized gas, entrapped therein, is added to the blood stream. As the saccharide dissolves in the blood stream, the individual microbubbles are released into the blood stream. The thus-generated microbubbles can be used to obtain an enhanced ultrasonic echographic image of a liquid containing the microbubbles. When the pressure in the cavities is different from the pressure in the blood stream, ultrasonic signals are produced on formation of the microbubbles, which can be used to measure local blood pressure. Although these microbubble precursors do not require the special storage treatment required for the precursors of U.S. Pat. No. 4,276,885, the number of microbubbles per unit volume of precursor which can be produced is inherently limited because of technological considerations.

While some of the prior art microbubbles, particularly the gelatin microbubbles and the microbubbles formed from the solid precursor, can be made relatively small, e.g., 10 microns mean size or even less, it is relatively more difficult and time consuming to make them in such a size range and requires the use of specialized equipment and carefully controlled parameters. This increases their cost and the very small gelatin microbubbles present storage difficulties because of their relatively short lifetime. Moreover, the number of microbubbles which can be generated in a liquid by microbubble-containing precursors is inherently limited to the number of microbubbles present in the precursor. Because the volume of precursor which can be added to a liquid is sometimes limited, e.g., in blood for physiological reasons, and both the number of microbubbles per unit volume of precursor which can be formed therein and the average size thereof are limited by technological factors, the echogenic opacification of liquids which can be achieved by such microbubble-containing precursors is less than optimum.

It would be desirable if a solid microbubble precursor could produce microbubbles in a liquid and especially in blood having a very small average diameter, e.g., about 10 microns, or less, in amounts greater than can feasibly be produced in a gel or solid microbubble-containing precursor.

It is an object of this invention to provide novel solid microbubble precursors which have the aforesaid microbubble producing capability. It is another object to provide solid microbubble precursors which are cheaper to produce than the solid precursors of U.S. Pat. No. 4,265,251. Still another object is to provide novel compositions of matter and articles of manufacture comprising such solid microbubble precursors.

A further object is to provide methods of producing such solid microbubble precursors and methods for generating microbubbles in liquids employing these solid microbubble precursors. Other objects will be apparent to those skilled in the art to which this invention pertains.

SUMMARY OF THE INVENTION

In a composition of matter aspect, this invention relates to a sterile injectable composition of matter adapted to generating microbubbles in blood consisting essentially of substantially microbubble-free, gas-containing aggregates of microparticles of a solid non-toxic physiologically acceptable material which is soluble in blood. In another composition of matter aspect, this invention relates to a suspension of said aggregates in a non-toxic physiologically acceptable liquid vehicle in which the aggregates and the gas contained therein are at least temporarily stable.

In an article of manufacture aspect, this invention relates to sealed containers containing a unit dosage amount of said aggregates and said carrier separately or as a suspension of the former in the latter.

In a method aspect, this invention relates to a method of altering the transmission characteristics of a liquid to an electromagnetic or elastic wave transmitted therethrough to produce a detectable signal, by dissolving in the liquid an amount of a particulate solid of this invention or a suspension thereof in a carrier liquid of this invention effective to form in the liquid an amount of microbubbles effective to substantially alter such transmission characteristics of the liquid in the area thereof containing the microbubbles. In a preferred aspect, the opacity of the liquid to ultrasonic waves is measured. In another method aspect, this invention relates to the injection of a composition of matter of this invention into the blood-stream of a living being to form microbubbles therein for diagnostic purposes.

In a further method aspect, this invention relates to methods of producing the solid microbubble precursors of this invention.

BRIEF DESCRIPTION OF THE DRAWING

The drawing is a greatly enlarged view of a preferred solid microbubble precursor 1 of this invention as a suspension in a carrier liquid 3 and consisting of an aggregate 5 of microparticles 7 of the solid precursor having surfaces 9 with gas absorbed therein and intracrystalline gas 15 entrapped in the microparticles. The aggregate has interconnecting passageways 11 between the microparticles communicating to the interior of the aggregate, which has interparticle entrapped gas 13 in voids therein.

DETAILED DISCUSSION

The present invention will be described specifically for ultrasonic imaging of the blood stream as a prime illustration of its use. Its similar use for imaging other liquid-containing vessels and chambers of the body altering the transmission characteristics of other liquids to electromagnetic and other sonic (elastic wave) waves transmitted therethrough, will then be obvious to those skilled in the art, as will be the use of the microbubble precursors to echogenically opacify or otherwise modify a physical characteristic of various liquids.

When utilizing the composition of matter and/or method of the present invention, a cloud of very small microbubbles of substantially uniform size, generally 10 microns or smaller in diameter, can be produced in liquids such as the blood stream of a living being, preferably a human being. Further, so many of these microbubbles are produced that in an ultrasonic image of the portion of the blood stream which contains these microbubbles, the blood stream can appear, if desired, to be opaque, i.e., an ultrasonically opaque cloud of the microbubbles can be formed which tends to completely fill the blood vessel. If desired, a lesser concentration of microbubbles can be formed by reducing the amount of microbubble precursor injected into the blood stream. That is, the density of the cloud of microbubbles can be controlled by controlling the amount of microbubble precursor which is added to the blood stream. This provides far better contrast and contrast control than is normally available with prior art microbubbles. The ultrasonic images can be used for quantitative diagnostic purposes, for determining blood flow rate, and the like, as described in U.S. Pat. No. 3,640,271; 4,265,251 and 4,276,885, whose disclosures are incorporated herein by reference.

Because the microbubbles formed in accordance with the present invention can substantially completely fill the blood vessel through which they are flowing, wall effects can be observed in the blood vessel, i.e., the degree of turbulence near the walls of the vessel and the inner structure of the walls can be observed. Additionally, the very small microbubbles formed can pass through capillaries, thus providing ultrasonic contrast enhancement even in capillary systems and without fear of gas emboli. Tiny right to left shunts in the heart are visible in ultrasonic images of the heart, since the small microbubbles can flow through such shunts. Small left-to-right shunts can also be detected, since the effluent sides of such shunts are clear of microbubbles.

It has been found that under certain conditions, a solid microbubble precursor need not have microbubbles, i.e., tiny balls or spheres of gas completely surrounded by solid, present therein in order for microbubbles to form in a liquid when the precursor is dissolved therein. All that is required is that the precursor provide an environment in the liquid in which it is dissolved which permits a plurality of microbubbles to form in the liquid and continue to exist for a finite period of time after their formation.

In order for any microbubbles to form in a liquid in which a microbubble precursor is dissolved, there must of course be a source of gas which provides the volume of gas needed to form the microbubbles. Heretofore, that source has been the gas in the microbubbles present in the precursor itself. These microbubbles are merely transferred from the precursor to the liquid in which it is dissolved. However, the gas can be supplied from one or more of (a) gas present in voids between the microparticles of the solid precursor aggregates; (b) gas adsorbed on the surfaces of the particles of the precursor; (c) gas which is an integral part of the internal structure of the particles of the precursor; (d) gas formed when the precursor reacts chemically with the liquid and (e) gas dissolved in the liquid and which is released therefrom when the precursor is dissolved therein. It was first believed that the latter was the primary source of the gas. However, it is presently believed that in many instances the gas in the microbubbles produced according to this invention comes predominantly from voids between the microparticles of the aggregates of the precursor and from surface adsorbed gas rather than from the liquid in which the precursor is dissolved, as evidenced by experiments in which the solid microbubble precursor of this invention which has been carefully degassed (under a vacuum) is added to a liquid which is saturated with gas. In such experiments, the degassed precursor produced far less microbubbles in the liquid than the same precursor prior to degassing. Because the gas-saturated liquid was unchanged, it cannot be the sole source of the gas in the microbubbles. In another experiment, when the microbubble precursor (without degassing) is added to the same liquid which has been carefully degassed, microbubbles are formed therein, although again in significantly lesser quantities than the same liquid prior to degassing. The latter experiment confirms that the precursor itself is a significant if not the predominant source of the gas in the microbubbles formed. That a lesser quantity of microbubbles are formed can be explained either by the degassed liquid no longer being an augmenting source of the gas for the microbubbles or by the degassed liquid being a poorer environment than a gas saturated liquid for the survival of microbubbles after they are formed, as explained hereinafter. Present evidence suggests the latter.

As stated above, a further requirement for a plurality of microbubbles to be formed according to this invention is that the microbubble precursor provide an environment in the liquid in which it is dissolved which permits the microbubbles to continue to exist in the liquid for a useful period of time, e.g., one or more seconds, after their formation. This requirement is met if the amount of precursor which is dissolved in the liquid in the area immediately surrounding each microbubble at the instant of its formation and thereafter during its useful lifetime is sufficient to render that area of the liquid supersaturated with respect to the gas in the microbubble. The required degrees of supersaturation must be sufficient to compensate for the elevated pressure within the microbubble arising from its surface tension, as will be described. If this requirement is not met, a 10 micrometer or less diameter microbubble will collapse in less than a second by dissolution in the liquid along with the precursor. Thus, the microbubble precursor must have sufficient mass to achieve this localized supersaturation.

Finally, if the number of microbubbles produced are to exceed significantly the number of particles of solid precursor which are added to the liquid, each particle must provide a plurality of nuclei for microbubbles to from. As explained hereinafter, aggregates of microparticles of the solid precursor provide such plurality of nuclei.

The aforesaid requirements can be met by a variety of solids, provided the solids have the requisite physical structure. This requisite physical structure can be determined from the criteria explained hereinafter.

Microbubble formation according to this invention is determined by the following factors:

1. The total volume of the microbubbles produced is equal to the sum of the volume of gas supplied by the solid precursor plus the gas precipitated from the surrounding liquid by solvation of the solid precursor.
2. The total number of microbubbles produced equals the total number of microbubble nuclei supplied by the solid precursor.
3. The size of each microbubble is determined by the volume of gas which is accessible to each bubble nucleus.
4. The life of the microbubbles is determined by the length of time that the microbubble precursor can achieve localized gas supersaturation of the liquid in the area surrounding each microbubble. Thereby preventing the microbubble from dissolving in the liquid.

Each of the foregoing will be discussed hereinafter.

I. SOURCE OF GAS FOR MICROBUBBLE FORMATION a. Total Volume of Gas Available for Microbubble Formation

The volume of gas $V_g$ introduced when a solid microbubble precursor dissolves in a liquid can be calculated as follows:

$$V_g = V_c + V_a + V_i + V_r$$

where
$V_c$ = volume of gas in the interparticle cavities between the microparticles of an aggregate precursor,
$V_a$ = volume of gas adsorbed on the surface of the microparticles,
$V_i$ = volume of intra-crystalline gas in the microparticles, and
$V_r$ = volume of gas produced by chemical reaction of the precursor with the dissolving liquid.

The total final volume $V_b$ of the gas available to form microbubbles is this gas volume $V_g$ introduced by the solid precursor plus the volume of dissolved gas $V_d$ precipitated from the liquid by solvation of the solid precursor, i.e., $$V_b = V_g + V_d$$

In the preferred embodiments of this invention $V_c > V_d > V_a > V_i$ and $V_r = 0$.

Stated another way, the total final volume of the microbubbles is $V_b = (\pi/6) ND^3$ where D is the final average diameter of the microbubbles, and N is the total number of bubble nuclei (and of microbubbles).

The origin and relative magnitude of each of these component gas sources will now be described.

b. Inter-Particle Entrapped Gas

Microparticles of a solid can adhere together into aggregates through electrostatic, chemical or physical bonding. When the interstitial space between the microparticles is filled with a gas, in the right environment the gas is released as microbubbles when the aggregates are dissolved in a liquid. The total amount of entrapped gas $V_c$ depends on the size distribution, shape and degree of compaction of the microparticles constituting the aggregates. The rate of solution of the aggregate, and therefore the bubble production rate, also depends on these geometrical properties as well as on the solubility of the constituent microparticles. The dependence of the size and number of interstitial cells on these geometrical properties of the aggregates is well known because of its importance in the production and properties of concrete. Under many conditions, this gas is the major source of gas for microbubble formation in the process of this invention.

c. Intra-Crystalline Entrapped Gas

Various methods of producing crystalline solids (single or polycrystalline) can cause a volume of gas $V_i$ to be entrapped within individual crystals (crystallites) or in the grain boundaries between the crystallites. Since pockets of this intra-crystalline gas can be formed by nucleation of gas molecules trapped (sorbed) in the lattice, the gas pressure in such pockets can be much higher than the pressure at which the gas was introduced into the solid, and much higher than that in the bubbles they form. The microbubbles formed when such a solid is dissolved in a liquid near atmospheric pressure therefore can be much larger than the size of the intra-crystalline gas pockets, can have much greater echogenicity, and the energy released upon bubble formation can vigorously agitate the liquid, including generation of ultrasonic sound impulses. Also the intra-crystalline entrapped gas can be a different gas than the gas present in the voids between the microparticles of the aggregates of the microbubble precursor. The latter volume of gas is substantially greater than the volume of intra-crystalline entrapped gas in the preferred precursors of this invention.

d. Surface Adsorbed Gas

Gas can be adsorbed on the surface of the microparticles of the aggregates of a microbubble precursor. When the microparticles are very small, the total surface area becomes very large, and the volume $V_a$ of adsorbed gas released can be substantial compared with the volume $V_p$ of the aggregate. It is readily shown that $V_a/V_p = \pi kT/pd^2D_p$ where k is the Boltzmann constant, T is temperature, p is the pressure of the gas in the microbubbles, d is the thickness of the layer of gas molecules adsorbed on the surface of the particles in the aggregate, and $D_p$ is the average diameter of the particles. For T = 300° K., p = 1 atm, and d = 3.6A (the diameter of the oxygen molecule), this equation gives $V_a/V_p \approx 1.0\ D_p$, for $D_p$ in micrometers. Therefore, an aggregate of 1 micrometer diameter microparticles having a complete single layer of gas molecules adsorbed on its surface could yield a volume of microbubbles about equal to the volume of the aggregate, and an aggregate of 0.1 micrometer particles would produce a tenfold larger volume of microbubbles when it dissolves.

Although a closely packed aggregate of very small microparticles can theoretically supply a large volume of adsorbed gas, the preferred microbubbles of this invention are loosely packed aggregates and the voids between the microparticles thereof are the major source of the gas supplied by the preferred precursors.

e. Gas Produced by Reaction With the Liquid

If the microbubble precursor undergoes a chemical reaction to form a gas when dissolved in a liquid, e.g., if microparticles of sodium bicarbonate are included in the aggregate, the volume of gas $V_r$ thus formed can contribute to the gas for the microbubbles. However, the preferred precursors of this invention merely dissolve in the liquid without undergoing a gas-forming chemical reaction. Therefore, $V_r$ usually is 0.

f. Gas Dissolved in the Liquid

When a solid soluble in a liquid saturated with dissolved gas is dissolved in the liquid, molecules of the dissolved solid can combine with molecules of the solvent liquid, reducing the concentration of the solvent and causing the liquid to become supersaturated with gas. Such molecular combination of a solute with its solvent is generally termed "solvation" ("hydration" in aqueous solutions), and the resulting decrease in gas solubility is termed "salting out". If the solvated liquid contains nuclei for the formation of gas bubbles, gas will precipitate from solution onto these nuclei to form bubbles. This phenomenon is readily seen when salt or sugar is added to a carbonated beverage. If the number of such nuclei and their distribution in the liquid are in correct proportions, the gas will form microbubbles of the required size in the liquid. The volume of gas precipitated from such liquids $V_d$ usually contributes significantly to the volume of gas in the microbubbles produced according to the process of this invention, either additively with the gas supplied by the microbubble precursor, or by reducing the amount of the latter gas which dissolves in the liquid during microbubble formation. If the microbubble precursor provides only the nuclei for the microbubbles and little or no gas, e.g., a degassed precursor containing insoluble bubble nuclei, the gas in the liquid can be predominant or even the sole source of gas for the microbubbles. Conversely, if the liquid is completely degassed, it can supply none of the gas.

The fraction of the dissolved gas which is precipitated from a volume $V_L$ of a gas-saturated liquid via solvation (salting out) by a mass M of solid precursor is $$e = \frac{\Delta a}{a} = K \frac{M}{V_L}$$

where $a$ is the Bunsen absorption coefficient (cm$^3$ of dissolved gas per cm$^3$ of liquid), and K is the solvation factor of proportionality. The volume of precipitated gas therefore is $V_d = V_L \Delta a$.

II. MICROBUBBLE NUCLEI

It is shown below that in order to achieve the greatest echogenic capability for a given amount of gas it is necessary to achieve the smallest practical bubble diameter. Microbubbles less than 10 micrometers in diameter, i.e., near capillary diameter, are also desirable physiologically since they should be non-hazardous if they pass from the venous to the arterial system. Furthermore, additional resonance enhancement of echogenicity (more than 10-fold) can be obtained at typical megacycle ultrasonic imaging frequencies if bubbles in this size region are used.

It can be shown from the above equations that to achieve a given desired microbubble diameter D, the number of bubble nuclei per unit mass of solid precursor $n = N/M$ must be $$n = \frac{6}{\pi D^3 d} \left( \frac{V_g}{V_s} + aKd \right)$$

where $V_s$ and d are the volume and density of the solid precursor, respectively. If it is assumed that there are $\epsilon$ nuclei associated with each microparticle of mass $M_p$ in the aggregate, the ratio of particle diameter to bubble diameter must be $$\frac{D_p}{D} = \left( \frac{\epsilon}{\frac{V_g}{V_s} + aKd} \right)^{\frac{1}{3}}$$

III. REQUIREMENT FOR BUBBLE STABILITY

The lifetime of microbubbles of the desired small size usually is very short in gas-saturated water or blood. For example, the lifetime of a 10 micrometer diameter nitrogen bubble in nitrogen-saturated water or blood is only about 1 second, and that of a 1 micrometer bubble is only a few milliseconds. The degree of gas supersaturation e in a liquid which is sufficient to prevent microbubbles of the required size D from dissolving in the liquid over a useful period of time is given by $$e = \frac{\Delta a}{a} = \frac{4t}{Dp}$$

where t is the surface tension of the liquid-gas interface and p is the saturation pressure of the dissolved gas in the liquid.

In the present invention, this required degree of supersaturation is obtained by solvation of a mass M of solid precursor in the region of liquid of volume $V_L$ containing the microbubbles. The above equation plus the equation defining the fraction of the dissolved gas which is precipitated from a volume of a gas-saturated liquid therefore requires for stability that $$\frac{M}{V_L} = \frac{4t}{DpK}$$

IV. ULTRASONIC PROPERTIES OF MICROBUBBLES

The ultrasonic scattering cross-section of each microbubble is $\sigma = D^2 F_r$, where $F_r = \{[(D_r/D)^2 - 1]^2 + \delta^2\}^{-1}$ where $D_r$ is the resonant bubble diameter and $\delta$ is the damping constant. For air bubbles in water, $D_r=650/f$ cm at frequency f and $\delta\simeq0.2$. when $D>>D_r$, $F_r\simeq1$, and when $D\simeq D_r$, $F_r\simeq25$.

The ultrasonic echogenicity of the microbubbles per unit mass of solid precursor, viz., $E=n\sigma$, therefore is given by $$E = \frac{6F_r}{Dd}\left(\frac{V_g}{V_s} + \alpha Kd\right)$$

Therefore, for a given gas solubility $\alpha$ and a given mass M of solid precursor of density d, more ultrasonic contrast can be produced by a small bubble diameter D, a large fraction of entrapped gas $V_g/V_s$, a high solvation factor K, and operation near bubble resonance.

V. SUMMARY OF REQUIREMENTS FOR THE MICROBUBBLE PRECURSOR AND QUANTITATIVE EXAMPLES THEREFOR

The following conditions are essential for forming and retaining microbubbles of a given required diameter which are useful for an appreciable time in a liquid with a given initial gas content:

(a) Sufficient gas must be available in the microbubble precursor and in the volume of liquid $V_L$ to provide the total volume $V_b$ of microbubbles giving the required ultrasonic echogenicity in the volume $V_L$.

(b) A sufficient number of gas nuclei n must be provided by the microbubble precursor to produce the required diameter D of microbubbles with the available volume of gas $V_b$.

(c) Sufficient mass M of solid must be present in the microbubble precursor to supersaturate the volume of liquid $V_L$ with gas by solvation such that bubbles of the required diameter D do not dissolve during the required period of use.

Condition (a) requires sufficiently high values of entrapped gas fraction $V_g/V_s$ and solvation factor K, which together are required physical and chemical properties of the precursor.

Condition (b) requires a number of gas nuclei which is consistent with Condition (a) and the required microbubble diameter D, and which is primarily a required physical property of the precursor.

Condition (c) requires a sufficient concentration of solid precursor $M/V_L$ which is dependent primarily on the ratio t/K of surface tension t to solvation factor K, both of which can be affected by the chemical properties of the solid precursor and its carrier liquid.

The following set of values are typical for the various physical and chemical properties of solid precursors useful for microbubble ultrasonic image enhancement:

In water, $\alpha=0.029$ for $O_2$, 0.015 for $N_2$ and 0.76 for $CO_2$ at 25° C. and one atm. partial pressure each. In venous blood, for which the $O_2$, $N_2$ and $CO_2$ partial pressures respectively are about 40, 760 and 45 torr, $\alpha\simeq0.06$. For ionic salt solutions, see P. S. Albright and J. W. Williams, Trans. Faraday Soc. 33, 247 (1937), $K\simeq300$ Z/W cm$^3$/g, where Z and W are the valence and atomic weight of the salt. If $V_g$ equals the void volume in an aggregate of spherical particles, $V_g/V_s=0.35$, 0.9, and 1.9 for closepacked, simple-cubic and diamond arrays, respectively. For gas adsorbed on particles of $D_p$ micrometers in diameter, $V_g/V_s\simeq1/D_p$.

As a typical example relative to echogenicity, for $D=10$ micrometer bubbles, and dextrose or galactose as solid precursors with $d=1.5$ g/cm$^3$, $W=180$ g, $Z\simeq1$, $V_g/V_s\simeq1$ and $\alpha=0.06$, the above formulas give for non-resonant ultrasonic echogenicity in venous blood $$E=4\times10^3 [1+0.15] \text{ cm}^2/\text{g}.$$

For these conditions, therefore, it can be seen that a very large echogenicity is obtained per gram of solid precursor, of which about 15% arises from precipitated gas. For a close-packed aggregate of effectively divalent solid precursor, however, precipitated gas would contribute about half or more of the total echogenicity.

Relative to the required nuclei, if each interparticle cavity in an array of spherical particles acts as a bubble nucleus, $\epsilon=0.75$, 1.0, 1.5 respectively for body-centered, close-packed and simple-cubic arrays. It follows from the above formulas that the required particle diameter is about equal to the desired bubble diameter, e.g., $D_p/D=(1.5/1.15)^{1/3}=1.1$. It has been found that efficient production of microbubbles less than 10 micrometers in diameter by a solid precursor requires a precursor particle size in this range. It can be seen from the foregoing that non-wetting solid nuclei of this number and diameter rather than gas entrapped in the solid precursor can be used as microbubble nuclei, provided that the solid precursor and the liquid in which it is dissolved collectively provide the volume of gas needed for a stable microbubble formed at the site of the nuclei.

Relative to the required mass of solid precursor, for blood $t\simeq42$ dyne/cm, so that the above formulas give for $p=1$ atmosphere and $D=10$ micrometer bubbles, $M/V_L=0.10$ g/cm$^3$.

It has been observed that an $M=1.5$ g injection of galactose solid microbubble precursor is about optimum for enhancement of an ultrasonic image of a dog heart, for which the above calculated example give a final volume of blood-galactose mixture of $V_L=15$ cm$^3$. The ventricular stroke volume for the dog is in the 15–25 cm$^3$ range. It appears, therefore, that the solid precursor injection is carried as a bolus into the ventricle where it is nearly completely mixed with blood.

From the foregoing, it can be seen that bubble production by a solid microbubble precursor can be improved by any or all of the following means:

(a) Increasing the volume of gas precipitated from the liquid, e.g., by the use of a strongly solvating compound as solid precursor, or of more precursor;

(b) Increasing the amount of gas entrapped in a given mass of the precursor, e.g., by reducing the size and/or packing density of the microparticles in aggregates forming the precursor;

(c) Increasing the number of bubble-forming nuclei (consistent with a and b), e.g., by reducing the size of the microparticles or by adding a non-wetting nucleating agent thereto;

(d) Reducing the amount of precursor required to achieve the requisite degree of localized gas supersaturation in the liquid in which the precursor is dissolved; by the use of a rapidly-dissolving strongly-solvating compound as precursor, by adding the precursor as a mixture with another liquid or solid which reduces the solubility of the gas dissolved in the gas-saturated liquid or by producing a low bubble surface tension, e.g., by the inclusion of a small amount of surfactant in the solid precursor or its carrier liquid;

All of the previously-described processes probably are active to various degrees in a good solid microbubble precursor. However, the production of localized gas-supersaturation in the liquid surrounding the microbubbles is essential.

PRODUCTION AND OBSERVED BEHAVIOR OF SOLID MICROBUBBLE PRECURSORS a. Commercially-Available Salts and Saccharides

A variety of salts and saccharides in their commercially available form have been evaluated as solid precursors for microbubble production. Visual observations of microbubble formation correlate well with quantitative measurement of the ultrasonic contrast effect produced by any given material. For samples consisting of relatively large individual crystals, with no visual evidence of entrapped gas, their behavior is consistent with the gas precipitation (salting out) aspect of microbubble production.

It has been confirmed by quantitative experiments that the smaller the particles, the more effective is a given material as a solid microbubble precursor. This is consistent with the gas precipitation mechanism because the greater rate of solution of a finely-divided material should result in a higher degree of local gas supersaturation and, therefore, in a greater production rate and total number of microbubbles for a given quantity of material. Materials estimated to have good solvation tendencies were shown to have the best microbubble production characteristics. Microbubble production in degassed water by precursors which are highly active in gas-saturated water, and in gas-saturated water by degassed (in a vacuum) precursors that were highly active therein prior to degassing, is substantially less, which confirms that the solid precursor and the test liquid collectively must supply enough gas to provide stable bubbles. Since the test liquids and microbubble precursors are rarely degassed, this requirement can readily be met.

PHYSICAL FORM OF SOLID MICROBUBBLE PRECURSORS a. Optimum Physical Form

The microbubble precursors of this invention, unlike those of U.S. Pat. Nos. 4,265,251 and 4,276,885, are themselves substantially free of microbubbles, i.e., microspheres or balls of gas completely surrounded by the precursor material.

The microbubbles are generated by the solid precursors of this invention by their formation in the liquid in which the precursor is dissolved. Like the precursors of U.S. Pat. No. 4,265,251, the present precursors are stable solids at ambient temperatures and are non-toxic and physiologically acceptable when injected in the blood stream of a living being, e.g., a human.

The physical structure of the microbubble precursor is extremely important and determines the number and size of the microbubbles produced therefrom. A precursor in microcrystalline form whose crystals are discrete, compact, and relatively free from structural defects have few nuclei for forming microbubbles and therefore little bubble generating capacity, e.g., as little as one bubble or less, per particle, whereas aggregates of particles having a plurality of internal voids communicating with the exterior of the aggregate are the most effective. Aggregates of microparticles, each microparticle having an average size corresponding approximately to the size of the microbubbles desired, are preferred.

The number of particles in each aggregate is preferably greater than 10 in order to achieve an appreciable volume of internal structure in the aggregate, and is more preferably greater than 100 such as to approach the advantages of a fully-developed aggregate structure. The preferred size of microparticles in the aggregate is about equal to the microbubble size which is optimum for the intended application and falls in the range of 1 to 50 micrometers. Most preferably, however, the microparticle diameter falls in the range of 5 to 10 micrometers since this size range of bubbles is most useful for injection in the bloodstream, as described previously.

The preferred size of the aggregate of microparticles is most often determined by the optimum dissolving time of the precursor for a given application. For example, if bubble generation is required immediately after injection at the injection site, an average aggregate size of about 20 micrometers is preferred, whereas for enhancing the ultrasonic image of the right heart it is found that a 40 micrometer average size is preferable, and for traversing the lungs to image the left heart it is found that a 125 micrometer average size is preferable. For general use, aggregates in the 30–50 micrometer size range is most preferable.

It is clear, however, that the preferred average microparticle and aggregate sizes are subject to certain constraints. For example, the microparticle size must be consistent with the preferred number of particles for a given aggregate size, or vice versa, depending on which requirement, i.e., bubble size or dissolving time, is dominant in the specific use of the precursors. Also, to obtain the desired average aggregate sizes, it may be necessary to pass the precursor through a screen so that particles larger than about 250 micrometers are not present and the precursor can freely pass through an injection needle.

Because the solid precursor is ordinarily the primary source of the gas for the microbubbles, the voids in the aggregates ordinarily and preferably contain a volume of gas corresponding approximately to the volume of gas in the microbubbles produced by the precursors although, as explained hereinabove, this is not vital if the liquid is gas-saturated.

In addition to the physical structure of the particles which must provide the requisite plurality of microbubble nuclei, the mass of the precursor must be sufficient to render the regions of the liquid in which it is dissolved immediately surrounding the site where a microbubble forms and is subsequently used to become supersaturated with respect to the gases dissolved therein, or expressed another way, in quasi-equilibrium with respect to the gas in the microbubble. It usually is insufficient for the liquid to merely be saturated with gas at the ambient pressure of the liquid because the pressure of the gas in the microbubble ordinarily substantially exceeds the ambient pressure of the liquid due to surface tension effects. Therefore, in order for a microbubble to have a useful life after it forms in the liquid in which the precursor dissolves, the liquid must be supersaturated with respect to ambient pressure to the same degree that the pressure of the gas in the microbubble exceeds the ambient pressure.

The overpressure in the bubble due to surface tension is inversely proportional to the bubble diameter, and is about one atmosphere for a 3 micrometer bubble in water. Therefore unless this overpressure in the bubble is compensated by a similar overpressure in the dissolved gas, the large pressure difference and large surface-to-volume ratio will cause microbubbles in this size range to dissolve in the liquid immediately after they are formed, or even before the gas nuclei are released from the aggregate.

The solid precursor of this invention provides both the gas nuclei and the solid mass required to stabilize the resulting microbubbles by solvation-induced supersaturation of a liquid. The mass to gas volume ratio $M/V_g$ for the precursor required to produce, stabilize and augment microbubbles of a given diameter depends on the ratio $t/K$ as defined in the previous analysis. The surface tension $t$ and the solvation factor $K$ both are dependent on both the properties of the liquid and of the solid, so that for a given liquid the required mass to gas volume ratio depends on the properties of the solid. As discussed below, it has been found that the bubble generating properties of different solid materials in the same aggregate form can vary widely, but that the best biocompatible solid materials have bubble-generating properties in the above-described optimum aggregate precursor form which are essentially similar and which are highly effective for producing ultrasonic contrast in the blood stream. The preferred mass to gas volume ratio of these materials, not including gas outside of the aggregates, is obtained when the density of the aggregate is in the range of ⅛ to ⅝ of the bulk density $d$ of the solid. Most preferably, the density of the aggregate is about $d/2$, such that the average size of the interparticle voids is about equal to the average size of the microparticles which in turn is about equal to the desired size of the microbubbles produced by the precursor. For the saccharides $d \simeq 1.5$ g/cm$^3$, and for NaCl, $d = 2.17$ g/cm$^3$.

Although it may appear to be difficult to provide all of the conditions necessary to produce microbubbles of the required size in useful quantities and with a useful life, a wide variety of the microbubble precursors of this invention can readily produce these conditions if the criteria discussed above are met. The criteria for an acceptable microbubble precursor can be determined theoretically, as discussed hereinbefore.

It was found that the same solid material obtained from different commercial sources or pulverized by different methods can have remarkably different microbubble production characteristics because they depart in various ways from the optimum physical form described above. In order to obtain the high reliability, reproducibility and effectiveness required for clinical diagnosis, it was therefore necessary to establish methods of preparation of standard solid microbubble precursor materials which are independent of the form of the raw starting material and which result in the optimum physical form. It has been found that such standard materials can be produced from commercially-available starting materials by carefully controlled ball-milling into a finely-divided powder or by controlled recrystallization.

b. Ball-Milling

Commercial lots of a variety of saccharides selected for potential biocompatibility were ball-milled for 10 minutes of a Pitchford Chemical Model 3300 ball mill with three 1.5 cm diameter alumina balls. The resulting powders are aggregates of microparticles, the aggregates being in the 1–160 micrometer size range, with aggregates near 40 micrometers predominating, and the microparticles being in the 1–20 micrometer range with microparticles near 10 micrometers predominating. The 1 micrometer lower limit is the resolution limit of the light microscope used. Although a large number of smaller microparticles and aggregates could also exist, they would not occupy a significant fraction of the total volume of powder. Relatively few of the largest aggregates occur and these also occupy an insignificant volume. They can be removed by screening, if desired.

Among the saccharide precursors produced by this preparation procedure, galactose was found to give the best ultrasonic contrast in all ranges of particle size obtained by screening. It was selected as the standard material for a series of in vitro or in vivo tests.

Since a large amount of interparticle entrapped gas exists in loose aggregates of fine particles of these materials, a significant contribution of such gas to their microbubble production is possible.

Heating and extensive plastic working of the material occurs during the milling process. Diffusion of air into the hot material, or entrapment of air during plastic working, can occur in this material, such that a contribution by intra-crystalline entrapped gas to its microbubble production characteristics is possible. Since a significant fraction of the material consists of particles less than 10 micrometers in diameter, contribution of adsorbed gas to microbubble production also could be significant. Finally, the great amount of plastic working, along with the possibility of gaseous and solid inclusions inherent to the milling process, should provide a high density of bubble forming nuclei in this material.

Although gas precipitation (salting out) is a significant effect with these materials, they also produce some bubbles when dissolved in degassed water. The volume of microbubbles produced therein is much less, however, which suggest that the totality of the other effects, e.g., of gas entrapped in the voids between microparticles, also is a significant if not predominant factor.

c. Water Recrystallization

Galactose was found to be distinctly superior to dextrose and sodium chloride as a solid microbubble precursor for producing ultrasonic contrast when prepared by the ball-milling method. However, dextrose and NaCl are preferred as biological contrast agents because their suitability for injection in large quantities into the blood stream is well-established, whereas the universal suitability of galactose is less certain. Methods have been found for preparing highly active dextrose and NaCl microbubble precursors which are comparable to or superior to the galactose prepared by the ball-milling method.

The first of these methods, most suitable for dextrose and other materials which tend to decompose upon heating to high temperatures, involves the recrystallization of dextrose from a saturated aqueous solution at low temperatures. Commercial USP dextrose is dissolved in boiling deionized water to obtain a saturated solution which is rapidly cooled by stirring in an ice water bath until recrystallization begins. The solution is then completely recrystallized for several hours in air at 6° C. and ambient pressure. The resulting crystals are washed with USP ethanol and dried in 25% humidity air at ambient pressure.

The resulting precipitate consists of large, i.e., ranging from about 100 to 1000 micrometers in size, relatively hard and dense aggregates of microparticles of dextrose averaging 5 to 20 micrometers in size. The aggregates dissolve relatively slowly in gas-saturated water and continuously evolve copious quantities of vigorously-expelled microbubbles in the 1–10 micrometer diameter range until they are completely dissolved.

When the aggregates are crushed, the resultant individual particles are in the 10–100 micrometer range and also evolve microbubbles in the same manner, but aggregates and particles much smaller than this dissolve without producing microbubbles. The rate of production and total number of microbubbles produced by the aggregates is much less in degassed water than in gas-saturated water, and the lifetime of the bubbles produced is less in the degassed water. The ultrasonic contrast obtained with this precursor is equal to or superior to ball-milled galactose.

The second recrystallization method is more rapid and is useful for materials like NaCl which can be heated to high temperatures. Commercial NaCl crystals are dissolved in a minimum amount of hot deionized water. The solution is then heated rapidly in a crucible maintained at a temperature which boils off all the water, preferably within about one minute. The remaining NaCl crystals are cooled immediately to room temperature. The visual appearance and microbubble production characteristics of this activated NaCl material are similar to those of the activated dextrose obtained by low temperature recrystallization.

d. Solvent Recrystallization

Another method for preparing standard microbubble precursors from commercially-obtainable materials does not produce more microbubbles than the water-recrystallized materials but has unique microbubble production characteristics which may be important in specific applications requiring these characteristics.

In this method, a solid precursor is dissolved in a hot organic solvent, e.g., dextrose is dissolved in boiling hot (80° C.) pure ethanol, and is recrystallized and dried in the same manner described for the low temperature water recrystallization method. Dextrose recrystallized by this method has a delicate dendritic structure and forms aggregates with a large open structure like fresh snow. This material dissolves instantaneously in water, leaving behind a "ghost" of relatively few microbubbles having a rather large range of sizes (10–100 micrometers) in the same shape as the aggregate.

e. Radiation Activation

Large crystals (1 to 0.1 mm) of the polysaccharide arabinose were observed to produce negligible microbubbles even in water supersaturated with $CO_2$. After irradiation with high energy cobalt gamma rays, this material produced copious quantities of 10 micrometer bubbles in $CO_2$-supersaturated water as it dissolved. This result indicates that crystal defects produced by the irradiation can serve as nuclei for the production of solvation-precipitated microbubbles. The other effects seem unlikely to be significant in this method.

CHEMICAL TYPES OF SOLID MICROBUBBLE PRECURSORS

For industrial uses, the solid precursor can be any solid having the requisite physical structure which is soluble in the liquid in which the microbubbles are formed. Since these liquids are almost always aqueous, the solid precursors ordinarily are materials which are soluble in water. High solubility is desirable because the degree of supersaturation achievable depends on the concentration of the solvating solid precursor that is achievable in the liquid. A 10% degree of supersaturation is marginally capable of stabilizing a 30 micrometer bubble, so that the preferred solubility is greater than the 0.3 mole/liter concentration of an effectively monovalent solid to which this degree corresponds. Solubilities equal to or greater than 1 mole/liter are preferable because such concentrations give more than 30% supersaturation, which can stabilize bubbles smaller than 10 micrometers.

Since there is an optimum dissolving time, however, there is an associated optimum rate of solution, which is proportional to the solubility, for the preferred aggregate sizes previously cited. For applications benefiting from a long dissolving time, such as for imaging the left heart, a low solubility is beneficial but it must be consistent with that required for adequate supersaturation described above. The optimum solubility for such applications therefore should be near 1 mole/liter. In fact, it has been found that galactose is superior to the other saccharides for producing left heart contrast and its solubility is about 1 mole/liter (0.20 g/cm$^3$).

Because the microbubble precursors are prepared prior to usage, for storage purposes they should be stable at ambient temperatures. For economic reasons, they preferably also are stable in air. Although crystalline compounds are preferred, amorphous compounds which form aggregates of microparticles of the requisite size can also be used.

The microbubble precursors can thus be formed of a number of chemicals or mixtures thereof. For example, various salts such as sodium chloride, sodium citrate, sodium acetate, and sodium tartrate are operable, provided they have the requisite physical conformation. Polyvalent electrolytes such as $CaCl_2$ and $AlCl_3$ are effective but are biologically less acceptable. Many organic and inorganic compounds are also useful as microbubble precursors, including those listed in the table below, of which glucose, galactose, maltose and sodium chloride are preferred. Other sugars and sugar related compounds which can be used include arabinose, maltotriose, maltotetrose, sorbitol, mannitol, gluconic acid and saccharide acid. Particularly useful organic compounds are the sugars which have the ability to hydrogen bond to water. Monosaccharides and disaccharides have been found to be excellent microbubble precursors. Raffinose, a trisaccharide, is also acceptable as a precursor. Table I shows sodium chloride and various sugars formed into microbubble precursors by the ball-milling technique which have been tested.

TABLE I

| Solid Precursor | *Largest Bubble Size, Micron |
|---|---|
| Galactose | 15 |
| Maltose | 25 |
| Lactose ("Fast Flow", Foremost Foods) | 20 |
| Lactose | 25 |
| Sucrose | 20 |
| Glucose (dextrose) | 20 |
| Sodium Chloride | 20 |
| Glucose, anhydrous | 20 |
| Raffinose | 25 |
| Fructose (levulose) | 25 |

*Microscopic observation of effect of adding water to a dispersion of the precursor in glycerol.

It should be noted that although the maximum bubble size (Table I) was 15–25 microns, the mean bubble size was about 10 microns. Such very small microbubbles have the ability to enter capillaries and provide ultrasonic contrast therein. Furthermore, many relatively small microbubbles form a very fine and dense contrast agent with substantially complete ultrasonic opacification of the lumen being possible. This allows, for example, the detection of small shunts and other small structures and flows in the heart. Further, because of the extremely efficient opacification obtained, more contrast can be obtained for the same amount of contrast agent than with prior art microbubble contrast agents. The degree of opacity (density) can be controlled by controlling the amount of solid precursor which is used. Furthermore, since different saccharides dissolve at different rates, and different salts at still different rates, the arrival time of microbubbles at any particular location in the blood stream can be regulated by selection of a particular saccharide or salt. Thus, any of a number of peripheral injection sites can be utilized to produce microbubbles at any one specific location in the blood stream, for example at the heart, by selecting a saccharide or a salt which dissolves at a particular rate. Different carrier liquids can also be used with a particular solid precursor to select the site of microbubble production. Still further, because of the very small microbubble size attainable, the microbubbles can traverse across the lungs when the contrast agent is injected on the venous side and therefore can provide contrast to the left side of the body. Because of the relatively small bubble size attainable, the dangers of air emboli are essentially eliminated. This size is small enough for safe passage through brain capillaries, for example, and allows enhancement of ultrasonic images of brain blood vessels.

CARRIER LIQUID

In a preferred embodiment of the invention, the solid microbubble precursor is added to the liquid in which the microbubbles are to be supplied as a dispersion or suspension in a carrier liquid in which the solid precursor is at least transiently stable, i.e., it is chemically and physically stable therein and does not form all of its micobubbles therein for at least several seconds after being dispersed therein, preferably for at least several minutes or longer.

The carrier liquid has several important functions:

(a) It acts as a dispersant, allowing the solid precursor powder to be formed into and uniformly dispersed throughout a stable or quasi-stable suspension suitable for injection into the bloodstream or other test liquid in which the microbubbles are to be generated.

(b) It serves to hold the solid precursor suspension therein together as a viscous bolus for transport within the test liquid to the site where the microbubbles are to be used.

(c) It serves as a surfactant to modify the surface properties of the test liquid so as to promote formation and stabilization of the very small microbubbles formed by interaction of the solid precursor with the test liquid.

Relative to its function as a dispersant, the carrier liquid must be adequately wet the solid precursor to form a uniform slurry, but must preserve and not substantially dissolve the aggregates of microparticles and the entrapped gas nuclei therein. It has been found that a number of gas-saturated non-aqueous carrier liquids, particularly those low polarity liquids which do not solvate the solid precursor and in which the solid precursor is insoluble, satisy these criteria. Relatively dilute aqueous solutions can also be used as carrier liquids but only if sufficient carrier liquid is used to form a dense slurry of the solid precursor. Although a small amount of precursor dissolves in the carrier liquid of such a slurry, the carrier liquid becomes saturated with the solid so that no further significant dissolution occurs. Furthermore, the high concentration of solid precursor in the carrier liquid causes it to be highly supersaturated with gas. Therefore, the gas nuclei in the solid precursor, or even microbubble nuclei partially released therefrom, are stable against dissolution. Still further, the viscosity of the slurry should be sufficiently high such that the suspended solid precursor and microbubble nuclei do not separate out of the suspension for a sufficiently long time between its formation and its injection. In in vivo usage, the viscosity of the slurry must be sufficiently low for ease of injection. The ability to use water as the primary constituent of the carrier liquid is important for use in the bloodstream in order to minimize potential adverse physiological effects of other materials. Only enough such other materials should be added to obtain the required wetting and surfactant properties of the carrier liquid; e.g., 5% propylene glycol in water is found to be a satisfactory carrier liquid. When used with ball-milled galactose precursor, for example, this carrier liquid forms a slurry which is sufficiently stable for injection up to an hour after it is formed without appreciable loss of bubble-generating effectiveness.

Relative to its function as a transport assisting medium, the carrier liquid mixed with the solid precursor in the prescribed proportion forms a slurry which is sufficiently viscous to prevent its significant mixing with the test liquid during its transport in the test liquid to the site where the bubbles are to be generated and used. It is found that the optimum viscosity of the slurry depends on the distance from the point of injection to the point of microbubble use. The viscosity of the slurry can be adjusted by varying the amount of carrier liquid relative to the amount of solid precursor or by varying the amount of non-aqueous dispersing agent in a given amount of carrier vehicle. For example, it has been found that a volume of 5% propylene glycol aqueous solution as carrier liquid which gives optimum ultrasonic right heart imaging with easy injectability, also is easily injected when the same volume of more viscous 10% propylene glycol aqueous solution is used, which is superior for left heart imaging.

Relative to the function of the carrier liquid as a surfactant, the importance of a low surface tension to the formation and stabilization against dissolution of very small microbubbles has already been emphasized. Another aspect of importance is the role of a surfactant in preventing the coalescence of the small microbubbles to form physiologically-undesirable large bubbles. An important criterion in selection of a carrier liquid is therefore the degree to which it lowers the surface tension and suppresses bubble coalescence.

To achieve together the above-identified functions, the preferred viscosity of the slurry formed with the carrier liquid and solid precursor is in the range 5–30 centipoise, with about 15 centipoise being the most preferable for general purposes. For in vivo usage, a viscosity no greater than 1,000 cps ordinarily is required. Apparently bubbles formed with a surface active carrier liquid retain a layer of surfactant molecules on their surface, preserving low surface tension and anticoalescence even after the slurry is dispersed in the test liquid at the test site.

Table II lists a number of liquids which have been tested as carrier liquids by first mixing them with a specific microbubble precursor (ball-milled galactose) to form a dispersion, and then adding water and observing any microbubble formation. The rankings are from zero to ten, with higher numbers indicating increased microbubble formation for equal amounts of galactose. The listing in Table II is not exhaustive of all possible carrier liquids, but is rather exemplary of the fact that a large number of dissimilar liquids can serve as the carrier liquid. Such liquids as dimethylacetamide, glycerol formol, glycofurol, benzyl benzoate, various oils, and various dioxolanes, for example, are useful as carrier liquids, at least for some solid precursors. Although methanol and ethanol are operable, they take only a few minutes to inactivate the galactose. Hence, only very fresh dispersions of galactose in these carrier liquids are useful for microbubble formation.

Carrier liquids are useful in in vitro liquid situations to regulate the concentration of microbubbles produced per unit volume of test liquid by increasing the volume of test liquid in which the solid precursor is dispersed before it dissolves therein. Because of the efficacy of the microbubbles produced according to this invention in altering the transmission characteristics of a liquid to elastic and electromagnetic waves, substantially less solid precursor is required to significantly alter those characteristics than prior art sources of microbubbles.

TABLE II

| Carrier Liquid | Microbubble Ranking Visual[1] | | Opacification Ultrasonic[2] |
|---|---|---|---|
| | Immediate | After 5 Minutes | |
| Alcohols | | | |
| Methanol | 7 | 0 | 8 |
| Ethanol | 9.5 | 1 | 9 |
| Propanol | 9.5 | 9.5 | 9 |
| Isopropanol | 9.5 | 9.5 | |
| Butanol | 9.5 | 9.5 | |
| Pentanol | 9.5 | 9.5 | |
| Hexanol | 9.5 | 9.5 | |
| Heptanol | 9.5 | 9.5 | |
| Octanol | 9.5 | 9.5 | |
| Carbitol | 9.5 | 9.5 | |
| Polyols | | | |
| Ethylene glycol | 4.5 | 2 | |
| Polyethylene glycol 400 | 9 | 9 | 6 |
| Propylene glycol | 9.5 | 3.5 | 4 |
| β-propylene glycol | 3.5 | 1.5 | |
| Glycerol (96%) | 8 | 8 | |
| Glycerol (99.5%) | 9.5 | 8.5 | 7 |
| 1,4-butanediol | 8.5 | 7.5 | |
| Carboxylic Acids | | | |
| Acetic | 9.5 | 8.5 | |
| Benzoic | 9.5 | 9.5 | |
| Esters | | | |
| Corn oil | 9.5 | 9.5 | |
| Peanut oil | 9.5 | 9.5 | |
| Sesame oil | 9.5 | 9.5 | 5 |
| Ethyl oleate | 9.5 | 9.5 | 8 |
| Isopropyl myristate | 9.5 | 9.5 | 7 |
| Ethers | | | |
| Diethyl ether | 1 | 1 | * |
| Tetrahydrofuran | 6 | 1 | |
| Mixtures | | | |
| Polyvinyl pyrrolidone/ethanol 1:1 | 8.5 | 7.5 | 9 |
| 1:2 | 8.5 | 7.5 | 9 |
| Glycerol/ethanol; 1:1 | 8.5 | 3.5 | 9 |
| Glycerol/saline; 1:4 | | | 8 |
| Polyethylene glycol/ethanol; 1:1 | | | 8 |
| Polyethylene glycol/isopropyl myristate; 1:1 | | | 8 |
| Sesame oil/isopropyl myristate; 1:1 | | | 6 |
| Polyethylene glycol/oleate; 1:1 | | | 4 |

*Anomalous results obtained as diethyl ether is itself vaporized into large bubbles.
[1]Visual observation of microbubbles formed in a dispersion of about 60 mg. of solid precursor in about 0.1 ml. of carrier liquid after a drop of 21% glycerol in saline was added thereto.
[2]Ranking in flowing system, observation of ultrasonic image (Immediate injection of dispersion of solid precursor in carrier liquid)

It is not necessary that the carrier liquid be soluble in blood. Although sesame oil, corn oil peanut oil and other triglyceride esters of fatty acids are not significantly water (or blood) soluble, they are excellent carrier liquids. Basically, although they wet and coat the precursor aggregates, apparently the shear stresses within the blood stream, and the dynamics within the heart, serve to physically erode these triglyceride esters off of the microbubble precursor, which then dissolves in the blood and provides the desired plurality of microbubbles. This is particularly desirable in that the triglyceride ester coating can keep the microbubble precursor from producing most of the microbubbles until it has reached, for example, the heart, where erosion is greatest.

Some of the carrier liquids of Table II were also tested using recrystallized glucose and either recrystallized or ball-milled sodium chloride as the microbubble precursor. Whereas ball-milled sodium chloride was inferior to ball milled galactose as a microbubble precursor, recrystallized glucose and sodium chloride were as good as or superior to the galactose.

For use in the body, both the carrier liquid and the microbubble precursor must be biocompatible, i.e., non-toxic and non-allergenic and otherwise physiologically acceptable in the amount injected. As is obvious, only some of the liquids (or liquid mixtures) in Table II satisfy this criterion.

Aqueous solutions are suitable as carrier liquids for injection into the blood stream, provided the solution is viscous enough to prevent instantaneous formation of all of the microbubbles upon mixing the microbubble precursor with the carrier liquid. Such aqueous solution preferably has a viscosity substantially greater than water, preferably at least 5 and no more than 1,000 centipoise. Suitable materials for increasing the viscosity of aqueous carrier liquids include glycerol, propylene glycol, polyethylene glycol 300 and 400, polyvinylpyrriolidone and other water dispersible polymers, preferably those which are biocompatible as defined above.

It is also desirable that the microbubble precursor have a bulk density approximately equal to that of the carrier liquid so that a stable dispersion is maintained. This can be attained by use of a mixture of liquids having one component that is more dense and another component which is less dense than the bulk density of the microbubble precursor.

ARTICLES OF MANUFACTURE

In one article of manufacture aspect, the preferred non-toxic, physiologically acceptable solid precursors of this invention are provided in sterile unit dosage form, i.e., about 0.25 to 10 and preferably about 0.5 to 3.5 grams, sealed in a container with access means thereto, e.g., a conventional glass vial with separable neck portion, a capped bottle, a flexible plastic pouch or a conventional vial with an opening sealed by a membrane of rubber or other elastomer through which a hypodermic can be inserted to mix carrier liquid with the solid precursor therein and remove the mixture therefrom after forming an homogenous dispersion of the latter in the former.

In another article of manufacture aspect, the aforesaid preferred solid precursors are supplied as a kit along with a separately sterile packaged, e.g., sealed in a glass vial, or in the cylinder chamber of a hypodermic, unit dosage amount, i.e., from about 0.25 to 10 ml., preferably about 1 to 7.5 ml., of a physiologically acceptable sterile carrier liquid therefor as defined hereinabove in which the solid precursor is at least temporarily stable therein, i.e., after mixing therewith either microbubbles do not form in significant amounts or they continue to form for at least several minutes.

In a further article of manufacture aspect, sterile unit dosage amounts of the solid precursor and carrier liquid are supplied in separate compartments of a single sealed two-compartment vial having means to mix the ingredients within the vial. Such vials are conventional and are disclosed in U.S. Pat. Nos. 2,694,614; 2,908,274; 3,073,471; 3,081,899; 3,464,414; 3,940,003 and 4,089,432, whose disclosures are incorporated herein by reference. Preferably, the two-compartment vial has an elastomeric plug between the upper and lower compartments which can be pierced by a hypodermic needle or which can be forced, by increasing the gas pressure in the upper compartment, into the lower compartment. The vial has an elastomeric cap which can be pierced by a hypodermic needle and which is covered by a removable dust cover. The solid precursor is stored in the lower compartment and the carrier liquid is stored in the upper compartment. To form a suspension of the solid precursor in the carrier liquid, the dust cover is removed and, if the plug can be forced into the lower compartment, it is done so by injecting air into the upper chamber with a hypodermic needle or by otherwise increasing the pressure therein, e.g., by forcing the elastomeric cap inwardly into the upper chamber. If the plug is adapted to be pierced by a needle, the hypodermic needle is inserted through the elastomeric cap, the carrier liquid is drawn into the hypodermic, the needle inserted through the plug and the carrier liquid expelled into the lower chamber. After forming a uniform dispersion or suspension of the solid precursor in the carrier liquid, the mixture is drawn into the hypodermic and injected into the test liquid to form microbubbles therein.

TEST LIQUIDS

The relatively high polarity liquid to which the microbubble precursors of this invention are added to form and stabilize microbubbles therein by solvation generally has a quite high dielectric constant (above 40) and generally will be an aqueous liquid, such as blood with a dielectric constant of approximately 80. It is essential that the carrier liquid not significantly interfere with solvation (polar or hydrogen bonding coordination) of the test liquid with the solute formed by dissolving the solid microbubble precursor therein. This assures that the water concentration in the test liquid locally will be reduced whereby gas dissolved in the test liquid will be precipitated out or the solubility in the test liquid for gas supplied by the solid precursor will be reduced. A highly polar carrier liquid can be used if, as previously described, its properties are such that the solid precursor is prevented from completely dissolving therein before the mixture is added to the test liquid.

METHODS OF USE

The compositions of this invention can be used to alter the transmission characteristics, i.e., either reflectivity or absorptivity of electromagnetic and sound (elastic wave) radiation transmitted through a liquid in order to produce a detectable signal, by providing the liquid with an amount of microbubbles effective to substantially alter the transmission characteristics of such radiation through the liquid in the area thereof containing the microbubbles.

Because microbubbles generally alter the physical properties of liquids that affect the transmissibility and reflectivity of electromagnetic and sound (elastic wave) radiation incident on a region of the liquid containing the bubbles, the compositions and articles of manufacture of theis invention are useful in a variety of analytical, diagnostic and operational procedures, as will be apparent to those knowledgeable in imaging, detecting, ranging and testing through the use of such radiation. Examples of such electromagnetic properties of a liquid which can be altered by microbubbles are: resistivity, electric and magnetic susceptibility, dielectric constant and absorption, nuclear and electron paramagnetic resonant response. Examples of elastic wave properties which can be altered are: compressibility, density, acoustic impedance and absorption. Examples of such radiation and the associated uses which can potentially benefit from the use of the microbubble generation compositions and articles are: medical and industrial ultrasonic imaging (both transmission and echographic), X-ray imaging (e.g., CT scanning), NMR imaging, microwave imaging, and marine sonar. Furthermore, alteration of the pressure wave transmissivity and reflectivity of water by microbubbles can be used to direct or deflect explosive pressure waves in the ocean. Because the volume of microbubbles and the uniformity and reproducibility of number and size thereof which can be achieved in accordance with this invention, procedures involving microbubble technology which heretofore were not practical because of the expense and complexity of mechanical means or amounts of microbubble precursor required to produce the requisite amount and quality of such microbubbles are now feasible.

In accordance with one embodiment of the invention, a dispersion or suspension as described above is added to the blood stream, generally by injection, catheterization or the like. Thereafter, an ultrasonic image is obtained of the stream opposite a location where the carrier liquid has dissolved or dissipated and the solid precursor has dissolved and dispersed microbubble nuclei therein, thereby providing the blood with the required plurality of microbubbles. Blood flow rate can be determined by simultaneously measuring the positions and velocities of the microbubbles, or of the cloud of microbubbles, from such an ultrasonic image. Blood flow rate can also be determined by measuring the intensities of two ultrasonic images, one from a proximal wall and the other from a distal wall of a blood vessel, at a location in the blood stream and applying conventional dye dilution equations or by measuring the intensity from a distal interface prior to and during flow of the microbubble-containing liquid. Also, the boundary between the flowing blood and the blood vessel can be observed for evidences of turbulence which may be caused by plaque formation on the blood vessel walls.

In accordance with another embodiment of the invention, the microbubble precursor described above can be dissolved in a highly polar liquid, e.g., temporarily withdrawn blood, normal saline, or water, preferably in a syringe or the like, to form a cloud of microbubbles, and the polar liquid-microbubble cloud can be injected into the blood stream. The microbubble precursor can also be directly added to the liquid without a carrier liquid.

The aforementioned improvement has been shown to be particularly useful in enhancing ultrasonic images of the blood stream, i.e., of the cardiovascular system. Very superior ultrasonic contrast is obtained over any of the prior art microbubble contrast agents. The microbubbles formed are generally much smaller than those with prior art contrast agents and a very much higher concentration of such microbubbles can be formed for better contrast, with greater convenience and control, and at lower cost.

All of these advantages also can be obtained when this invention is used to enhance ultrasonic images of other liquid-filled regions of the body, such as the lymphatic, digestive, urinary, reproductive, bilary and other systems, as well as intra-peritoneal, intra-cranial, intra-thoracic and other body cavities and spaces. Furthermore, these advantages all apply to the enhancement of ultrasonic images of liquid-filled regions in medical and non-medical, (e.g., industrial) equipment and apparatus.

Similarly, because of the volume of microbubbles per unit mass of solid precursor which can be generated, the solid precursors of this invention can be used to alter the transmission characteristics to a variety of elastic and electromagnetic waves of large bodies of liquids, e.g., industrial product or waste water, sea water, city effluent water, to monitor flow rates, currents or solid body movement therein, etc., employing technology known in the microbubble art. As is apparent from the foregoing discussion, although microbubbles are ordinarily used to enhance the imaging of an electromagnetic or sonic radiation transmitted through a liquid, they can also be used to reduce or otherwise modify the signal produced by the generation of such radiation through a liquid.

Although at least a portion of the microbubbles are ordinarily formed in situ in the liquid through which a signal is transmitted, as will be apparent the microbubbles can first be formed in another liquid, e.g., a carrier liquid as defined herein, and the carrier liquid containing the microbubbles can then be added to the liquid in which the wave energy is transmitted, e.g., the blood stream of a living being. However, the life of such microbubbles therein is less than when the microbubbles are formed in situ.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

COMPOSITION OF MATTER

Example 1 Ball Milled Galactose

About 5 g (10 ml) of commercial d(+)-galactose (anhydrous powder) is placed in an alumina chamber, with alumina ends containing three ½-inch diameter alumina balls, while in a low humidity (20% RH) atmosphere. The above assembly is mounted in a Pitchford ball mill model 3800. The galactose is pulverized in the ball mill for 10 minutes, then removed from the chamber and stored in a low humidity (20% RH) room temperature (19°–29° C.) environment until use.

In contradistinction to the starting powder, which has virtually no microbubble forming capability, the ball milled galactose has a mean particle size of 45 $\mu$m, which particles are aggregates of microcrystals of a means size of 10 $\mu$m with voids between the microcrystals of about the same size which are highly active microbubble nuclei.

Example 2 Recrystallized Dextrose 15 g of commercial d-dextrose (monohydrate powder USP) is placed in a 100 ml glass beaker and wetted with 4.8 ml of hot (100° C.) deionized water. The beaker is heated in a water bath (100° C.) while its contents are stirred until all the dextrose crystals are dissolved. The beaker is cooled in an ice bath and the contents are stirred until crystals begin forming. The beaker is covered with plastic wrap and refrigerated (6° C.) for 12 hours.

The contents of the beaker are removed, placed on filter paper and washed with 100% ethanol. The crystals on the filter paper are placed in a low humidity (20% RH) atmosphere until dry (12 hours). The dry crystals are broken up using a mortar and pestle then sieved through a screen with 180 micrometer openings. The screened material is stored in a low humidity (20% RH) room temperature (19°–29° C.) environment until use.

The screened material, unlike the starting powder, has aggregates of an average size of 75 $\mu$m of microcrystals of a mean size of 10 $\mu$m with voids between the microcrystals of about the same size which are highly active microbubble nuclei.

Example 3 Recrystallized Sodium Chloride 10 ml of food grade NaCl (discrete crystals of 295 $\mu$m) dissolved in 20 ml of deionized water in a crucible. The crucible is rapidly heated until all the water is boiled off. The remaining crystals are then sieved through a screen with 180 micrometer openings. The screened material is stored at room temperature (19°–29° C.) until use.

The recrystallized NaCl has aggregates (58 $\mu$m mean size) of microcrystals (26 $\mu$m mean size) with voids between the microcrystals of about the same size which are highly active microbubble nuclei.

Example 4 Suspension of Solid Precursor in Carrier Liquid 10 ml of propylene glycol (PG) sterilized with dry heat (120° C., 4 hrs) is mixed with 90 ml of sterile, commercial 5% dextrose in water (D5W).

Add 1.5 g of the ball milled galactose of Example 1 to 3 ml of the thus-produced PG/D5W vehicle in a 50 ml polyethylene plastic beaker. Stir for about 15 seconds until the milky (with microbubbles averaging about 10 micrometers) mixture is homogenous. Draw the mixture into a sterile hypodermic and remove any entrapped air pockets. Use within about 10 minutes after mixing for optimum microbubble formation.

Follow the procedure of Example 4, using either a like amount of the recrystallized dextrose of Example 2 or the recrystallized NaCl of Example 3 to produce fluid mixtures having comparable microbubble generating capacities. Use within about 10 minutes after mixing for optimum microbubble formation.

ARTICLE OF MANUFACTURE

Example 5 Kit

Draw into a 10 ml plastic hypodermic syringe about 5.4 ml of the PG/D5W vehicle of Example 4 and cap the needle mounting neck of the syringe with a removable cap. Sterilize the sealed unit, e.g., by exposure to about 1.5 M rad of cobalt-60 gamma rays. Fill, under a dry nitrogen atmosphere, a 10 ml plastic pouch formed from flexible polyethylene film with about 2.7 g of the ball milled gallactose of Example 1, of the recrystallized dextrose of Example 2, or the recrystallized NaCl of Example 3. Seal the mouth of the pouch with a thin rubber membrane and cover the membrane with a metal lid and a crimp cover to hold the lid in place. Sterilize the sealed pouch, e.g., by exposure to about 1.5 M rad of cobalt-60 gamma rays. Package the syringe pouch as a kit, optionally along with a No. 16 sterile hypodermic needle.

In another version the plastic bag is replaced by a conventional rubber capped vial as described hereinabove. The solid precursor and vehicle are mixed by repeatedly transferring the mixture back and forth from the vial to the syringe.

Example 6 Method of Forming Microbubbles

To prepare a suspension of solid microbubble precursor in a carrier liquid of this invention using the kit of Example 5, remove the cap from the hypodermic syringe and sterile mount the needle thereon. Remove the crimp cover and lid from the mouth of the plastic bag, pierce the rubber membrane and expel the contents of the syringe into the bag. Manually mix the solid microbubble precursor with the liquid vehicle in the bag until a viscous milky (from microbubble formation) homogenuous mixture is formed. Withdraw the mixture from the bag into the syringe and use within about 10 minutes.

Example 7 Method of Using Microbubbles

Within a few minutes after formation of the suspension of galactose in PG/D5W vehicle as described in Example 6, make a bolus injection of 3 cc of the mixture containing 1.5 g of galactose precursor through an 18 to 14 gage plastic intracath into the femoral vein of a 25 to 40 kg dog. Follow injection immediately, through the same injection site, with a 10 ml bolus saline flush. During the contrast injection and saline flush, hand hold a conventional ultrasonic transducer, coupled with acoustic gel, against the right lateral chest wall of the dog at an intercostal space while the dog is lying on its right side. Record the signals M-mode and/or 2D echo contrast-enhanced ultrasonic images are obtained of the right heart which persist for ≈10 seconds.

The above procedure can also be followed employing 2.7 g of solid precursor in 5.4 ml of carrier liquid and an 18 ml saline flush, to obtain enhanced ultrasonic images of the right heart of humans, with the transducer hand held against the left chest wall of the patient at an intercostal or in the subxiphord position while the patient is supine.

Following the above procedure, the following ultrasonic image enhancements are obtained.

| Injection Site | Contrast Image | Solid Precursor | Carrier Liquid |
|---|---|---|---|
| Femoral Vein | Right Heart | 1.5 g | 3 ml |
| Right Heart | Right Heart | 1.0 g | 2 ml |
| Aorta | Aorta or Myocardium | 1.0 g | 2 ml |
| Left Heart | Left Heart or Aorta | 1.0 g | 2 ml |
| Intra-coronary | Myocardium | 0.5 g | 2 ml |

Example 8 Method of Using Microbubbles

The liquid in a pipe, or liquid leaking from a pipe into a surrounding liquid, is rendered substantially opaque to ultrasound by mixing 0.8 Kg of NaCl, recrystallized according to the procedure of Example 3, with one liter of gas saturated 10% aqueous propylene glycol and injecting the mixture into the test pipe at a rate such that about 10 liters of water flowing in the pipe mixes with each liter of injected mixture by the time the injected mixture reaches the region being tested. This region is then visualized by an ultrasonic imaging device, and the interior of the pipe, or the location and magnitude of microbubble-opacified water leaking from the pipe in the region, is determined in a manner which is well-known to those skilled in the use of such imaging devices. This permits examination of the interior of the pipe, or location and quantification of a leak in an apparatus such as a heat exchanger, without destroying or disassembling the pipe or apparatus, and to a degree not possible with prior art because of the small bubble size, high density, persistence and reproducibility obtainable with the material of this invention.

What is claimed is:

1. In a method for altering the transmission characteristics of a liquid to an electromagnetic or elastic wave transmitted therethrough by dispersing in the liquid an amount of microbubbles effective to substantially alter such transmission characteristics of the liquid in the area thereof containing the microbubbles, the improvement wherein the microbubbles are formed by dissolving in the liquid a solid which is particulate, is substantially free of microbubbles, and consists predominantly of particles which have a plurality of gas-filled voids communicating with the surface of the particles and a plurality of nuclei for microbubble formation and the ratio of the mass of the particles to the volume of gas in the voids is sufficient to render the liquid in which the particulate material is dissolved supersaturated with respect to the gas in the voids in the area of the liquid surrounding the microbubbles.

2. A method according to claim 1, wherein the liquid is aqueous.

3. A method according to claim 2, wherein the liquid is the blood stream of a living being and the particulate solid is non-toxic and physiologically acceptable in the amount dissolved therein.

4. A method according to claim 3, wherein the solid particulate material is glucose, galactose, maltose or sodium chloride.

5. A method according to claim 2, wherein the solid is added as a suspension in a carrier liquid in which the particulate material is at least temporarily stable.

6. A method according to claim 5, wherein the carrier liquid is aqueous and comprises a compound which increases the viscosity thereof.

7. A method according to claim 1, wherein the solid particulate material is predominantly aggregates of at least about 10 microparticles whose average size is from about 1 to 50 micrometers.

8. A method according to claim 7, wherein the liquid is the blood stream of a living being and the particulate solid is non-toxic and physiologically acceptable in the amount dissolved therein and is added thereto as a suspension in carrier liquid in which the particulate material is at least temporarily stable and which is non-toxic and physiologically acceptable in the amount added to the blood stream.

9. A method according to claim 8, wherein the carrier liquid is aqueous and the solid precursor is glucose, galactose, maltose or sodium chloride.

10. A method of enhancing ultrasonic images in the blood of a living test subject, comprising the steps of:
  (a) forming a fluid injectable suspension of:
    (i) a particulate solid which is non-toxic, physiologically acceptable material, soluble in blood and substantially free of microbubbles, whose particles are aggregates having gas filled voids therebetween of smaller particles having an average size in the range of from 1 to 250 micrometers, with the ratio of the mass of the smaller particles to the volume of gas in the voids therebetween effective to render blood in which the particulate solid is dissolved supersaturated with respect to the gas in the area of the blood surrounding the microbubbles when they form therein; in
    (ii) an amount of a carrier liquid which is non-toxic and physiologically acceptable and in which the particulate material is at least temporarily stable;
  (b) injecting a unit dosage amount of the fluid injectable suspension into the venous system of the test subject, thereby forming a cloud of microbubbles in the blood therein; and
  (c) obtaining an ultrasonic image of the blood opposite a location containing said microbubbles.

11. A method according to claim 10, wherein the solid particulate material is glucose galactose, maltose or sodium chloride.

12. A method according to claim 10, wherein the carrier liquid is aqueous and has a viscosity substantially greater than water.

13. A method according to claim 12, wherein the particulate solid is glucose, galactose, maltose or sodium chloride.

14. A method according to claim 10, including as an added step determining both the velocity and position of said microbubbles from examination of said ultrasonic image and calculating blood flow rate from said velocity and position measurement.

15. A method according to claim 10, including as an added step calculating blood flow rate from the intensities of two images measured at said location using dye dilution techniques.

16. A method of producing a sterile injectable composition of matter in unit dosage form and adapted for injection into the blood stream of a living being and generating microbubbles therein, comprising a particulate solid which is non-toxic, physiologically acceptable material, soluble in blood and substantially free of microbubbles, whose particles are aggregates having gas filled voids therebetween of smaller particles having an average size in the range of from 1 to 250 micrometers with the ratio of the mass of the smaller particles to the volume of gas in the voids therebetween effective to render blood in which the composition of matter is dissolved supersaturated with respect to the gas in the area of the blood surrounding the microbubbles when they form therein,
  comprising forming the solid into aggregates of at least about 10 particles whose average size is from about 1 to 50 micrometers.

17. A method according to claim 16, wherein the solid particulate material is glucose, galactose, maltose or sodium chloride.

* * * * *